United States Patent [19]

Melendy

[11] Patent Number: 4,637,388
[45] Date of Patent: Jan. 20, 1987

[54] TRACHEAL TUBE OBTURATOR WITH REVERSIBLE TIP

[75] Inventor: Clifford P. Melendy, North Andover, Mass.

[73] Assignee: Portex, Inc., Wilmington, Mass.

[21] Appl. No.: 661,093

[22] Filed: Oct. 15, 1984

[51] Int. Cl.⁴ .............................................. A61M 16/00
[52] U.S. Cl. ........................... 128/207.14; 128/207.15; 604/170
[58] Field of Search ...................... 128/207.15, 207.14, 128/200.26; 604/164, 165, 170

[56] References Cited

U.S. PATENT DOCUMENTS

| | | | |
|---|---|---|---|
| 724,913 | 4/1903 | Montgomery | 604/278 |
| 3,626,950 | 12/1971 | Schulte | 604/268 |
| 3,719,190 | 3/1973 | Avery | 128/785 |
| 3,996,939 | 12/1976 | Sheridan et al. | 128/207.14 |
| 4,502,482 | 3/1985 | DeLuccia et al. | 128/207.15 |

*Primary Examiner*—Henry J. Recla
*Attorney, Agent, or Firm*—Pearson & Pearson

[57] ABSTRACT

An obturator especially for use as a part of a tracheal tube assembly permits the tracheal tube to have a squared off, unbeveled, distal end with an annular, circular rim of predetermined diameter which easily passes through the vocal cords. The obturator has a soft, flexible tip of generally conical configuration with a blunt, rounded apex and a truncated conical flexible trailing skirt with an outer diameter greater than the outer diameter of the tube rim to shield it during insertion and permit smooth tube entry. The skirt folds, or inverts, toward the apex to enable withdrawal of the obturator through the bore of the tube. The distal end of the metallic rod of the obturator is swaged and pierced and the soft tip is molded thereon to assure against dislodgement.

6 Claims, 6 Drawing Figures

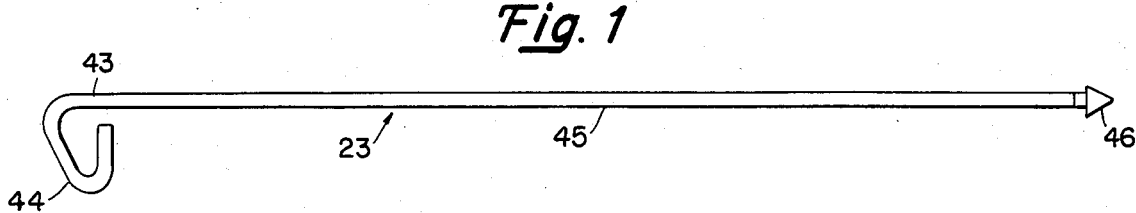
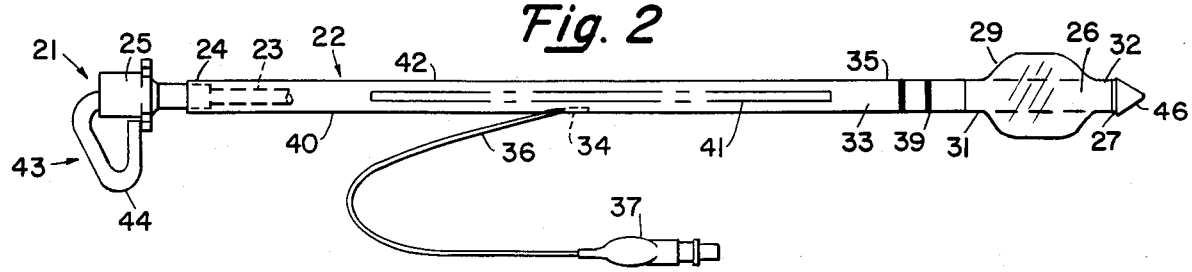
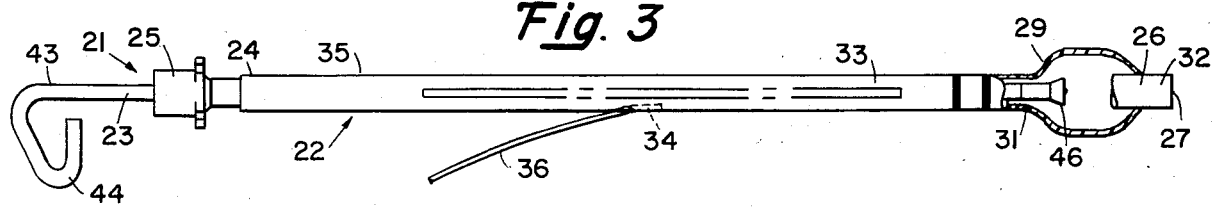
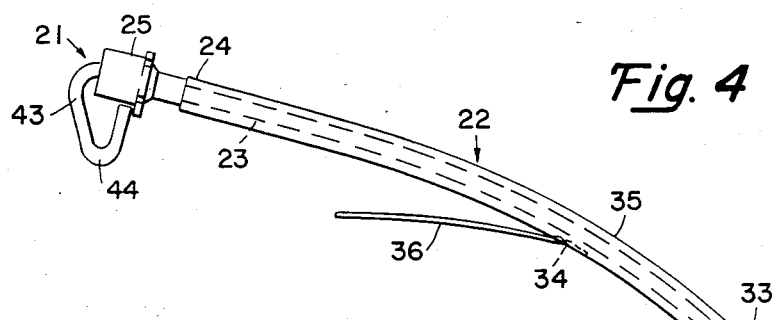
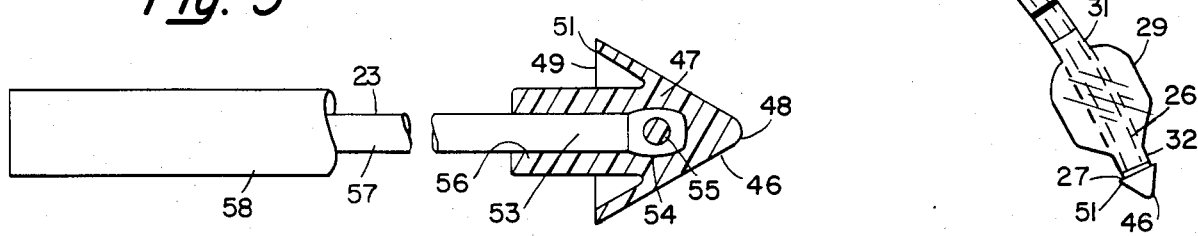
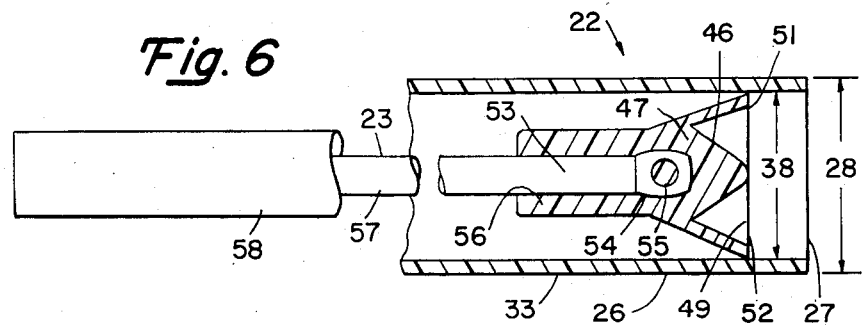

TRACHEAL TUBE OBTURATOR WITH REVERSIBLE TIP

BACKGROUND OF THE INVENTION

The American National Standard for anesthetic equipment, specifies the approved dimensions and configurations for tracheal tubes, including the angle of bevel at the patient, or distal, end, the location of the Murphy eye if used, the location of the balloon, or cuff, and its inflation tube, and the radius of curvature of the tube. Such tubes may be marked oral, nasal, or oral/nasal. Sharp points, or rough edges, on the patient end of the tracheal tube, on the bevel, or on the Murphy eye may cause mucosal damage and conventional stylets are used to provide smooth passage between the vocal cords in the throat.

It has long been known to use a conventional stylets to guide the distal end of a tracheal tube as it is inserted into a patient's mouth and down into the trachea such as disclosed in U.S. Pat. No. 3,659,612 to Shiley of May 2, 1972. The blunt rounded end of the obturator has the same outer diameter as the inner diameter of the bore of the tube, and the tube end is chamfered to produce a smooth surface and avoid gouging or cutting of any tracheal tissue with any sharp edges.

A similar bullet shaped guide is provided at the end of a stylet for inserting the inner end of a tracheal tube with nontraumatic insertion in U.S. Pat. No. 4,351,330 to Scarberry of Sept. 28, 1982.

In the syringe art, U.S. Pat. No. 724,912 to Montgomery of Apr. 7, 1903 discloses a syringe nozzle having an elongated straight hollow stem of hard rubber with a central passage for liquid and a disc at its discharge end formed of soft flexible material which is normally cup shaped, but adapted to fold in either direction to be inserted in, or withdrawn from, an orifice to be treated.

However, the Montgomery patent seeks only to seal against liquid pressure and its cup shaped disc while perhaps adequate to seal the rectum against the escape of liquid under pressure would be too flexible and flimsy to guide the distal end of a tracheal tube while smoothing the passage of the hard, open, distal end thereof.

SUMMARY OF THE INVENTION

In this invention the tracheal tube assembly includes a tracheal tube which preferably has a squared off, distal end, free of bevel, so that the inflatable cuff is closer to the end opening. The distal end, therefore, presents an annular, circular rim of predetermined outer diameter which is desired to be protected and covered by the soft flexible tip of the obturator to avoid damage to tracheal tissue while easing passage through the vocal cords.

The obturator of the invention is preferably formed of an elongated rod of bendable, metallic material, such as aluminum, enclosed in an extruded plastic sheathing, such as 80 Durometer P.V.C., and having a proximal, or machine, end with an integral handle. The distal, or patient end of the obturator is swaged and pierced so that the soft, flexible, resilient material, (preferably 55 Durometer Kraton a product of Shell, Inc.), of the conical tip, with its integral, trailing tube, may be molded around the rod and into the pierced hole therein.

The soft, flexible conical tip includes a blunt, rounded apex of predetermined axial length and an integral, hollow, truncated conical skirt about equal in axial length to the length of the apex, the skirt trailing behind the apex and having a trailing peripheral rim of predetermined outer diameter at least equal to the outer diameter of the rim of the distal end of the tube to abut thereon and cover the same.

When inserted in a tracheal tube the soft flexible tip of the obturator projects from the open end of the tube as a conical guide with the skirt forming a smooth surface with the exterior surface of the tube, and the rim of the skirt abutting the rim of the tube. After insertion, a withdrawal pull on the handle of the obturator causes the skirt to invert, or fold, forwardly toward the apex until the outer diameter reduces sufficiently to enable the soft, flexible reversible tip to be withdrawn through the bore of the tracheal tube.

The obturator may be packaged, shipped and stored with its elongated metallic rod straight, thereby reducing cost and space. When removed from its sterile package it may be easily bent into the approved curve of the tracheal tube, which is a radius of curvature of 14 CM±2 CM, and will retain that curvature while inserted in the tracheal tube and after withdrawal from the tube.

BRIEF DESCRIPTION OF THE DRAWING

FIG. 1 is a side elevation of an obturator with reversible tip of the invention;

FIG. 2 is a side elevation of a tracheal tube assembly of the invention, showing the obturator fully inserted in the tracheal tube, with the soft conical tip projecting from the open end;

FIG. 3 is a view similar to FIG. 2 showing the obturator slightly withdrawn, and partly broken away to show the tip inverted for withdrawal in the bore;

FIG. 4 is a view similar to FIG. 2, but showing the tube and obturator bent into a curve;

FIG. 5 is an enlarged, fragmentary, detail view showing the soft, flexible conical tip in half section on the swaged, pierced distal end of the rod; and FIG. 6 is a view similar to FIG. 5 showing the truncated conical skirt of the tip inverted toward the apex of the tip for withdrawal through the bore of the tube.

DESCRIPTION OF THE PREFERRED EMBODIMENT

In the drawing, 21 designates the tracheal tube assembly of the invention, including the tracheal tube 22 and the obturator 23.

The tracheal tube 22 has a proximal, or machine, end 24, with a 15 mm tracheal connector 25 inserted therein, a distal, or patient, end 26, with a squared off annular, circular rim 27, free of slant, bevel or Murphy eye, and preferably free of sharp points or rough edges. The annular circular rim 27 has a predetermined outer diameter 28 which varies with the length of the tube and the inside diameter of the tube as prescribed in the above mentioned American National Standard for anesthetic equipment, Tracheal Tubes—published by American National Standards Institute, Inc., 1430 Broadway New York, N.Y. 10018, 1983.

Tracheal tube 22 has an enlarged profile, inflatable cuff 29 with its opposite ends 31 and 32 sealed to the exterior surface 33 of the tube and the cuff is inflatable by the lumen 34 extending along the hollow tubular wall 35 of the tube and thence by the inflation line 36 to the pilot balloon 37 and a source of pressurized air not shown. Tracheal tube 22 has an elongated bore 38 of uniform diameter, and may be packaged, shipped and stored in straight configuration and bent into the desired curved configuration of FIG. 4 when about to be used. Locating rings such as at 39, a print area 41, such as shown in dotted lines, and a radio-opaque blue line 42, extending full length, may all be provided on the exterior surface 33 of the shank 40 of the tube 22.

The obturator 23 has a proximal, or machine, end 43, with an integral handle 44 which projects from the connector 25, an elongated, normally straight, shank 45, substantially equal in length to the length of the bore 38 and a soft flexible tip 46, of conical configuration, which normally projects beyond the distal end 26, and annular rim 27, of tracheal tube 22 when sleeved therein as shown.

The soft tip 46 is of resilient deformable flexible elastomeric material such as Kraton, preferably about 55 durometer, a product of Shell, Inc. and has a solid apex 47, with a blunt rounded tip 48, and a truncated conical, trailing integral skirt 49, the skirt and apex being about equal to each other in axial length as best shown in FIGS. 5 and 6. The skirt 49 has an outer rim 51 of predetermined diameter, 52 at least equal to the predetermined diameter 28 of the annular rim 27 at the distal end of the tube 22 so that it abuts the rim and covers it while forming a smooth surface merging with the exterior surface 33 of the tube 22.

As shown in FIGS. 3 and 6, the truncated conical skirt 49 inverts and folds forwardly toward the apex 47, with the rim 51 aligning with the tip 48, when the obturator is withdrawn through the bore 38 of the tube 22, thereby reducing its outer diameter.

The distal end 53 of obturator 23 is swaged flatwise as at 54 and pierced as at 55, and the tip 46 is provided with an integral tube 56 extending rearwardly therefrom and encircling the distal end 53 so that when the tip 46 is molded on the rod the molded material enters the pierced hole 55 to firmly anchor the tip against inadvertent dislodgement.

The obturator handle, shank and distal end is preferably a metallic, bendable rod 57 of aluminum enclosed in an extruded plastic sheathing 58 such as 80 Durometer P.V.C. As shown in FIGS. 1 to 3, the tube 22 and obturator 23 can be packaged, shipped and stored straight at low cost and bent into the curve shown in FIG. 4, at the point of use, the materials retaining the curve thereafter.

I claim:

1. A tracheal tube assembly comprising:
   a tracheal tube having a proximal end, an elongated bore of uniform diameter, and a distal end, said distal end terminating in an opening with an annular rim of predetermined outer diameter; and
   an obturator normally sleeved within the bore of said tube, but withdrawable therefrom, said obturator having a proximal end forming a handle, an elongated shank and a distal end with a soft, flexible, conical tip, mounting thereon and normally projecting from said tube opening and having an outer diameter at least equal to the outer diameter of said rim to shield, and cover the same during insertion of said assembly between the vocal cords;
   said soft tip being of resilient deformable material so as to be withdrawable through the bore of said tube with said obturator;
   said soft, flexible conical tip includes a blunt rounded leading apex of predetermined length and an integral trailing hollow skirt, of truncated conical configuration, said skirt being substantially equal in length to said apex and invertible toward said apex upon withdrawing of said obturator through said bore to reduce the diameter of said tip.

2. A tracheal tube assembly as specified in claim 1 wherein:
   the distal end of said tube having an annular rim which is squared off and free of bevel.

3. A tracheal tube assembly as specified in claim 1 wherein:
   said obturator is a normally straight rod of easily bendable metallic material, deformable into a curve and withdrawable from said tube when so curved.

4. A tracheal tube assembly as specified in claim 1 wherein:
   said obturator is a bendable metallic rod, covered with thermoplastic sheathing and having at least one pierced hole at the distal end thereof; and
   said soft tip is molded on the distal end of said rod, with its material anchored in said pierced hole and with an integral tube extending rearwardly therefrom and molded around said rod;
   whereby inadvertent dislodging of said tip is avoided.

5. An obturator for use in an indwelling device such as a tracheal tube, said obturator comprising:
   an elongated rod of bendable metal having a proximal end a handle and having a distal end forming a soft tip mounted on the distal end of said rod and being of conical outer configuration with a blunt, rounded apex, of predetermined axial length, and an integral, truncated conical hollow skirt, said skirt being substantially equal in axial length to said apex and of predetermined outer diameter, at least equal to the outer diameter of the indwelling device with which used, and being invertible toward said apex for withdrawing through the bore of any such device.

6. An obturator comprising:
   an elongated rod having a handle at one end and a flexible tip mounted on the other end, said tip being of conical configuration with a blunt rounded apex, a hollow integral, truncated conical skirt normally forming part of said conical configuration but being foldable and invertible toward said apex for withdrawal through a passage;
   said rod is of aluminum and is enclosed in a sheathing of thermoplastic, said rod being normally straight for shipment, but bendable into a curve when in use in a curved tracheal tube;
   said rod includes a distal end which is swaged flatwise and pierced with a hole; and
   said tip includes an integral hollow tube extending rearwardly therefrom and encircling the distal end of said rod;
   the tip and tube being molded on the distal end of said rod with the material thereof entering said pierced hole.

* * * * *